US009993428B2

(12) United States Patent
Gerard et al.

(10) Patent No.: US 9,993,428 B2
(45) Date of Patent: Jun. 12, 2018

(54) GASTRORETENTIVE DRUG FORMULATION AND DELIVERY SYSTEMS AND THEIR METHOD OF PREPARATION USING FUNCTIONALIZED CALCIUM CARBONATE

(71) Applicant: Omya International AG, Oftringen (CH)

(72) Inventors: Daniel E. Gerard, Basel (CH); Joachim Schoelkopf, Killwangen (CH); Patrick A. C. Gane, Rothrist (CH); Veronika Anna Eberle, Basel (CH); Rainer Alles, Basel (CH); Maxim Puchkov, Pfeffingen (CH); Jörg Huwyler, Arlesheim (CH)

(73) Assignee: Omya International AG, Oftringen (CH)

( * ) Notice: Subject to any disclaimer, the term of this patent is extended or adjusted under 35 U.S.C. 154(b) by 0 days. days.

(21) Appl. No.: 14/429,492

(22) PCT Filed: Oct. 10, 2013

(86) PCT No.: PCT/EP2013/071140
§ 371 (c)(1),
(2) Date: Mar. 19, 2015

(87) PCT Pub. No.: WO2014/057026
PCT Pub. Date: Apr. 17, 2014

(65) Prior Publication Data
US 2015/0231078 A1 Aug. 20, 2015

Related U.S. Application Data

(60) Provisional application No. 61/713,691, filed on Oct. 15, 2012.

(30) Foreign Application Priority Data

Oct. 12, 2012 (EP) ..................... 12188419

(51) Int. Cl.
*A61K 9/16* (2006.01)
*A61K 31/522* (2006.01)
*A61K 9/20* (2006.01)

(52) U.S. Cl.
CPC .......... *A61K 9/1611* (2013.01); *A61K 9/1617* (2013.01); *A61K 9/1641* (2013.01); *A61K 9/1652* (2013.01); *A61K 9/1682* (2013.01); *A61K 9/2009* (2013.01); *A61K 9/2013* (2013.01); *A61K 9/2031* (2013.01); *A61K 9/2054* (2013.01); *A61K 31/522* (2013.01)

(58) Field of Classification Search
None
See application file for complete search history.

(56) References Cited

U.S. PATENT DOCUMENTS

| | | |
|---|---|---|
| 3,418,999 A | 12/1968 | Davis |
| 3,976,764 A | 8/1976 | Watanabe et al. |
| 4,451,260 A | 5/1984 | Mitra |
| 4,702,918 A | 10/1987 | Ushimaru et al. |
| 4,814,179 A | 3/1989 | Bolton et al. |
| 6,666,953 B1 | 12/2003 | Gane et al. |
| 2001/0046473 A1* | 11/2001 | Besse .................. A61K 9/0007 424/44 |
| 2004/0020410 A1 | 2/2004 | Gane et al. |
| 2005/0202084 A1* | 9/2005 | Adusumilli et al. .......... 424/464 |
| 2008/0131506 A1* | 6/2008 | Cavalier ............. A61K 9/2009 424/465 |
| 2010/0151019 A1 | 6/2010 | Ramani et al. |

FOREIGN PATENT DOCUMENTS

| | | |
|---|---|---|
| AU | 737634 B2 | 11/1998 |
| BE | 839604 A1 | 3/1976 |
| CA | 2851069 A1 | 5/2013 |
| DE | 3527852 A1 | 2/1986 |
| EP | 0338861 A2 | 10/1989 |
| EP | 0717988 A1 | 6/1996 |
| EP | 2070991 A1 | 6/2009 |
| EP | 2168572 A1 | 3/2010 |
| JP | 6314715 A | 1/1988 |
| WO | 0039222 A1 | 7/2000 |
| WO | 2010037753 A1 | 4/2010 |
| WO | WO 2010/035273 * | 4/2010 ............... A61K 9/20 |
| WO | WO 2010/037753 * | 4/2010 ............... A61K 9/14 |

OTHER PUBLICATIONS

The International Search Report dated Nov. 11, 2013 for PCT Application No. PCT/EP2013/071140.
The Written Opinion of the International Searching Authority dated Nov. 11, 2013 for PCT Application No. PCT/EP2013/071140.
Extended European Search Report dated Dec. 17, 2012 for European Application No. 12188419.1.
Office Action dated Mar. 29, 2016 for Japanese Application No. 2015-536123.

* cited by examiner

*Primary Examiner* — Brian Gulledge
(74) *Attorney, Agent, or Firm* — Amster, Rothstein & Ebenstein LLP (57) ABSTRACT

An instantly floating gastroretentive drug formulation comprising at least one functionalized natural and/or synthetic calcium carbonate-comprising mineral and at least one pharmaceutically active ingredient and at least one formulating aid wherein said functionalized natural or synthetic calcium carbonate is a reaction product of natural or synthetic calcium carbonate with carbon dioxide and one or more acids, wherein the carbon dioxide is formed in situ by the acid treatment and/or is supplied from an external source.

21 Claims, 3 Drawing Sheets

GASTRORETENTIVE DRUG FORMULATION AND DELIVERY SYSTEMS AND THEIR METHOD OF PREPARATION USING FUNCTIONALIZED CALCIUM CARBONATE

CROSS-REFERENCE TO RELATED APPLICATIONS

This is a U.S. national phase of PCT Application No. PCT/EP2013/071140, filed Oct. 10, 2013, which claims priority to European Application No. 12188419.1, filed Oct. 12, 2012 and U.S. Provisional Application No. 61/713,691, filed Oct. 15, 2012.

FIELD OF THE INVENTION

The present invention relates to gastroretentive drug formulations and delivery systems using functionalized calcium carbonate and their method of preparation. The gastroretentive drug delivery system is instantly floating and can be in the form of a tablet, mini-tablet, granules, capsules or pellet. The gastroretentive drug delivery system is intended to remain in the stomach for a prolonged and predictable time delivering an active ingredient or inactive precursor. Instant flotation hereinafter implies zero lag-time before actual flotation takes place.

BACKGROUND OF THE INVENTION

In comparison to conventional dosage forms, gastroretentive drug delivery systems (GRDDS) are designed to remain in the stomach for a prolonged and predictable period of time. Consequently, gastric residence time of drug substances is extended and bioavailability improved. GRDDS are beneficial for a number of drugs, like drug substances whose site of action is locally in the stomach and drugs which exhibit a narrow absorption window in the stomach or in the upper part of the small intestine. Moreover, drugs which are degraded in the intestinal or colonic environment, as well as drug substances which are poorly soluble at alkaline pH-values are candidates profiting from GRDDS.

Various mechanisms have been proposed to achieve gastric retention and avoid unpredictable gastric emptying of dosage forms. These approaches include: co-administration of drugs or pharmaceutical excipients influencing gastric motility pattern and thereby delaying gastric emptying process, magnetic systems, mucoadhesive systems, size-increasing systems due to swelling or unfolding, density-controlled systems that either float on gastric contents or sediment, and combination systems.

Pawar et al. (Gastroretentive dosage forms: A review with special emphasis on floating drug delivery systems. Drug Delivery. 2011 February; 18(2):97-110.) considered floating drug delivery systems (FDDS) as an easy and logical approach regarding formulation and technical aspects for the development of GRDDS. FDDS are low-density systems with a density less than density of gastric fluids (~1.004 g/cm³). Therefore, dosage forms float on gastric contents and are retained in the stomach while releasing drug.

Since the idea of floating dosage forms was introduced by Davis in 1968 (U.S. Pat. No. 3,418,999), many research groups invented different strategies for preparation of FDDS. Floatation is achieved by incorporation of low-density materials, by swelling or by gas generation and entrapment. Due to the fact that excipients with density less than unity provide immediate floating to the delivery device, their use is highly favored for formulation development.

U.S. Pat. No. 3,976,764 discloses an instantly floating tablet, having a hollow sphere based on gelatin coated with several under-coatings, wherein an therapeutically active ingredient is comprised in one of the under-coatings.

DE 35 27 852 A1 discloses a pharmaceutical formulation with a specific density below 1, wherein a substance forming a gel in water is mixed with a pharmaceutically active ingredient and a fat/oil which is solid at room temperature. The gel forming substance being a cellulose-, dextran- or starch derivative.

EP 0 338 861 A2, refers to an antacid compositions with prolonged gastric residence time. The antacid such as Hydrotalcite or Amalgate forming a solid core which is surrounded by a solid external phase containing a hydrophobic substance e.g. an ester of glycerol with palmitic or stearic acid, hydroxylated polyalkene and a non-ionic emulsifier.

EP 0 717 988 A1, refers to a swollen molding which is an expanded structure having a mesh-like cross-section and an apparent density of less than 1, which structure is predominantly an acid-resistant polymer compound and additionally containing at least an auxiliary blowing agent and a drug substance. Because of its mesh-like structure in cross-section, the swollen molding of the invention has a multiplicity of microfine internal pores which are continuous or discontinuous. Said acid-resistant polymer compound are chosen, e.g. from hydroxypropylmethylcellulose acetate succinate or phthalate.

U.S. Pat. No. 4,451,260 refers to a multilayered structure comprising a pharmaceutical active ingredient wherein air is entrapped in the multilayered structure, thus promoting flotation.

U.S. Pat. No. 4,814,179 refers to a floating sustained release therapeutic composition. Non-compressed sustained release tablets comprise a hydrocolloid gelling agent, a therapeutically acceptable inert oil, the selected therapeutic agent and water.

The presence of pharmaceutically inert fatty materials having a specific gravity of less than one decrease the hydrophilicity and increase the buoyancy of the dosage form.

Optimal floating tablets have different conflicting characteristics. On the one hand, high porosity to float on stomach contents, on the other hand sufficient hardness to withstand destruction by gastric peristalsis. Further, high porosity having a positive effect on floating have at the same time also the disadvantage that when pores are exposed to the gastric fluid, water can enter the pores and fill them up and even propagate deeper into the pores, particularly when the pores are interconnected. As a consequence the inherent density will increase and thus decrease the floating capability of the tablet and thus provoking sinking of the tablet at a later stage, and bearing the risk of early clearing from the stomach by the know mechanisms such as peristaltic movements. Prior art counter acts this problem by including acids into their formulations in the presence of carbonates. The acids release $CO_2$ when in contact with water and by this effervescent mechanism, the tablets keep floating. The drawback however is, that such tablets are far more quickly dissolved and thus counteract the long residence time in the stomach.

The present invention provides thus for an instantly floating formulation with gastroretentive properties overcoming the drawbacks as currently presented.

The inventors surprisingly found out that particles from the paper industry can serve as novel pharmaceutical excipient exhibiting a highly porous meshwork with lamellar surface structure that grips particles strongly together. Due to its unique properties, functionalized calcium carbonate (FCC) is promising for preparation of FDDS. It offers the possibility to formulate them in to granules, pellets, capsules or to compact them into tablets or mini-tablets at a relative density of less than unity, i.e. less than 1.000 g/cm$^3$.

SUMMARY OF THE INVENTION

The functionalized natural and/or synthetic calcium carbonate (FCC) comprised in the gastroretentive drug delivery system, can be prepared from either natural ground calcium carbonate comprising mineral or from synthetic calcium carbonate, sometimes also named as precipitated calcium carbonate, or from blend of natural and synthetic calcium carbonates. The present invention also comprises a method of the preparation of the gastroretentive formulations and delivery systems.

The instantly floating gastroretentive delivery systems can be chosen from tablets, mini-tablets, granules or pellets. A further dosage form are capsules. Instantly floating as already indicated by its term float immediately on the surface of the gastric fluid after ingestion. Hence no activation of the floating mechanism is needed. The density of the instantly floating soluble gastroretentive delivery systems is below the density of the gastric fluid, which is around 1.004 g/cm$^3$. By this the initial floating properties as well as the floating properties during drug release from the gastroretentive formulation in the gastric fluid is maintained until complete dissolution of the gastroretentive formulation. These floating properties are achieved by formulating a functionalized calcium carbonate comprising mineral into an instantly floating gastroretentive formulation comprising at least one pharmaceutically active ingredient or inactive precursor, formulation aids and optionally further additives such as film forming substances, flavoring agents, lubricants, effervescent ingredients or colorants. Suitable ingredients being described in the prior art and comprised in the FDA list of food additives that are generally recognized as safe (GRAS), but not being limited to.

The present invention is further related to a method or process for manufacturing such a instantly floating and gastroretentive formulations, as well as its dosage forms.

The functionalized calcium carbonate comprising mineral together with the at least one active ingredient or inactive precursor together with granulating aids is dry or wet granulated by known methods. The granules can be dosed directly when being e.g. packaged in sachet or stick packs, or optionally compacted in to tablets, mini-tablets (i.e. tablets with diameter less than 3 mm) or pellets having a density below the density of the gastric fluid, e.g. a density below 1.000 g/cm$^3$. A further dosage form can also be in capsules.

DESCRIPTION OF THE INVENTION

The present invention relates to an instantly floating gastroretentive drug delivery system and to the method of their manufacture using functionalized calcium carbonate. The instantly floating gastroretentive drug delivery system of the present invention comprises a formulation for an instantly floating composition.

Said instantly floating gastroretentive formulation comprises at least one functionalized natural and/or synthetic calcium carbonate comprising mineral and at least one pharmaceutically active ingredient and at least one formulating aid, wherein said functionalized natural or synthetic calcium carbonate is a reaction product of natural or synthetic calcium carbonate with carbon dioxide and one or more acids, wherein the carbon dioxide is formed in situ by the acid treatment and/or is supplied from an external source.

Suitable amount of the functionalized natural or synthetic calcium carbonate comprising mineral are in the range of 30 wt % to 95 wt % based on the total amount of the composition.

Lower amounts could be used as well, however when made in to formulations the buoyancy might be affected in such way that the floating ability would be drastically decreased if not completely lost.

The source of natural calcium carbonate for preparing the functionalized calcium carbonate (FCC) is selected from the group of marble, calcite, chalk, limestone and dolomite and/or mixtures thereof.

In a particular embodiment the synthetic calcium carbonate for preparing the functionalized calcium carbonate is precipitated calcium carbonate (PCC) comprising aragonitic, vateritic or calcitic mineralogical crystals forms, especially prismatic, rhombohedral or scalenohedral PCC or mixtures thereof.

The process for preparing the functionalized natural and/or synthetic calcium carbonate (FCC) will now be further described.

In a preferred embodiment, the natural or synthetic calcium carbonate is ground prior to the treatment with one or more acids and carbon dioxide. The grinding step can be carried out with any conventional grinding device such as grinding mill known to the skilled person.

In a preferred process, the natural or synthetic calcium carbonate, either finely divided, such as grinding, or not, is suspended in water. Preferably the slurry has a content of natural or synthetic calcium carbonate within the range of 1 wt-% to 80 wt-%, more preferably 3 wt-% to 60 wt-%, and still more preferably from 5 wt-% to 40 wt-%, based on the weight of the slurry.

In a next step, an acid is added to the aqueous suspension containing the natural or synthetic calcium carbonate. Preferably, the acid has a pK$_a$ at 25° C. of 2.5 or less. If the pK$_a$ at 25° C. is 0 or less, the acid is preferably selected from sulphuric acid, hydrochloric acid, or mixtures thereof. If the pK$_a$ at 25° C. is from 0 to 2.5, the acid or its metal salt is preferably selected from H$_2$SO$_3$, HSO$_4^-$M$^+$, H$_3$PO$_4$, H$_2$PO$_4^-$M$^+$ or mixtures thereof, wherein M$^+$ can be Na$^+$ and/or K$^+$.

In another embodiment, the acid is preferably phosphoric acid in combination with acetic, formic or citric acid or acid salts thereof.

More preferably, the acid is phosphoric acid alone.

The one or more acids can be added to the suspension as a concentrated solution or a more diluted solution. Preferably, the molar ratio of the H$_3$O$^+$ ion to the natural or synthetic calcium carbonate is from 0.1 to 2.

As an alternative, it is also possible to add the acid to the water before the natural or synthetic calcium carbonate is suspended.

In a next step, the natural or synthetic calcium carbonate is treated with carbon dioxide. If a strong acid such as sulphuric acid or hydrochloric acid or a medium-strong acid is used for the acid treatment of the natural or synthetic calcium carbonate, the carbon dioxide is automatically formed. Alternatively or additionally, the carbon dioxide can be supplied from an external source.

Acid treatment and treatment with carbon dioxide can be carried out simultaneously which is the case when a strong acid is used. It is also possible to carry out acid treatment first, e.g. with a medium strong acid having a $pK_a$ in the range of 0 to 2.5, followed by treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the acid treatment step and/or the carbon dioxide treatment step are repeated at least once, more preferably several times.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the functionalized natural or synthetic calcium carbonate as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

Further details about the preparation of the functionalized natural calcium carbonate are disclosed in WO 00/39222 and US 2004/0020410 A1, wherein the functionalized natural calcium carbonate is described as a filler for paper manufacture, the content of these references herewith being included in the present application.

Yet a different process for the preparation of functionalized natural calcium carbonate suitable for the present invention is disclosed in EP 2 264 108 of the same applicant, the content of this reference being herewith included in the present application. Basically, the process for preparing a functionalized calcium carbonate in an aqueous environment comprises the following step:

a) providing at least one ground natural calcium carbonate (GNCC);
b) providing at least one water-soluble acid;
c) providing gaseous $CO_2$;
d) contacting said GNCC of step a) with said acid of step b) and with said $CO_2$ of step c);

characterized in that:
(i) said acid (s) of step b) each having a pKa of greater than 2.5 and less than or equal to 7, when measured at 20° C., associated with the ionisation of their first available hydrogen, and a corresponding anion formed on loss of this first available hydrogen capable of forming water-soluble calcium salts;
(ii) following contacting said acids(s) with said GNCC, at least one water-soluble salt, which in the case of a hydrogen-containing salt has a pKa of greater than 7, when measured at 20° C., associated with the ionisation of the first available hydrogen, and the salt anion of which is capable of forming water-insoluble calcium salts, is additionally provided.

The ground natural calcium carbonate is selected form the group consisting of marble, chalk, calcite, limestone and mixtures thereof. Suitable particle sizes of the GNCC can be easily found in the cited reference, as well as the water-soluble acids, e.g. particles with weight median diameter of 0.01 to 10 μm, and acids selected from acetic acids, formic acid, propanoic acid, and mixtures thereof.

The following examples are illustrative for the production of FCC's from different starting material.

Starting Material: Limestone

A calcium carbonate suspension is prepared by adding water and undispersed limestone (ground under wet conditions in water, optionally in the presence of a food approved dispersing or grinding aid such as Monopropyleneglycol (MGP)) having a $d_{50}$ of 3 μm, wherein 33% of particles have a diameter of less than 2 μm—in a 20-L stainless steel reactor, such that the aqueous suspension obtained has a solids content corresponding to 16 wt % by dry weight relative to the total suspension weight. The temperature of this suspension is thereafter is brought to and maintained at 70° C.

Under stirring at approximately 1000 rpm such that an essential laminar flow is established phosphoric acid in the form of a 30% solution is added to the calcium carbonate suspension through a separate funnel over a period of 10 minutes in an amount corresponding to 30% by weight on dry calcium carbonate weight. Following this addition, the suspension is stirred for an additional 5 minutes.

The resulting suspension was allowed to settle overnight, and the FCC had a specific surface area of 36 m²/g, and $d_{50}$ of 9.3 μm (Malvern) and $d_{98}$ of 23.5 (Malvern).

Starting Material: Marble

A calcium carbonate suspension is prepared by adding water and undispersed marble (ground under wet conditions in water, optionally in the presence of a food approved dispersing or grinding aid such as Monopropyleneglycol (MPG)) having a $d_{50}$ of 3.5 μm, wherein 33% of particles have a diameter of less than 2 μm—in a 20-L stainless steel reactor, such that the aqueous suspension obtained has a solids content corresponding to 16 wt % by dry weight relative to the total suspension weight. The temperature of this suspension is thereafter is brought to and maintained at 70° C.

Under stirring at approximately 1000 rpm such that an essential laminar flow is established phosphoric acid in the form of a 30% solution is added to the calcium carbonate suspension through a separate funnel over a period of 10 minutes in an amount corresponding to 30% by weight on dry calcium carbonate weight. Following this addition, the suspension is stirred for an additional 5 minutes.

The resulting suspension was allowed to settle overnight, and the FCC had a specific surface area of 46 m²/g, and $d_{50}$ of 9.5 μm (Malvern) and $d_{98}$ of 18.9 (Malvern).

Starting Material: Marble

A calcium carbonate suspension is prepared by adding water and undispersed marble of (ground under wet conditions in water, optionally in the presence of a food approved dispersing or grinding aid such as Monopropyleneglycol (MPG)) having a $d_{50}$ of 2 μm, wherein 48% of particles have a diameter of less than 2 μm—in a 20-L stainless steel reactor, such that the aqueous suspension obtained has a solids content corresponding to 16 wt % by dry weight relative to the total suspension weight. The temperature of this suspension is thereafter is brought to and maintained at 70° C.

Under stirring at approximately 1000 rpm such that an essential laminar flow is established phosphoric acid in the form of a 30% solution is added to the calcium carbonate suspension through a separate funnel over a period of 10 minutes in an amount corresponding to 50% by weight on dry calcium carbonate weight. Following this addition, the suspension is stirred for an additional 5 minutes.

The resulting suspension was allowed to settle overnight, and the FCC had a specific surface area of 71 m$^2$/g, and d$_{50}$ of 10.6 μm (Malvern) and d$_{98}$ of 21.8 (Malvern).

Similarly, functionalized precipitated calcium carbonate is obtained. As can be taken in detail from EP 2 070 991 B1 from the same applicant, wherein functionalized precipitated calcium carbonate is obtained by contacting precipitated calcium carbonate with H$_3$O$^+$ ions and with anions being solubilized in an aqueous medium and being capable of forming water-insoluble calcium salts, in an aqueous medium to form a slurry of functionalized precipitated calcium carbonate, wherein said functionalized precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by H$_3$O$^+$ ions, where said H$_3$O$^+$ ions are provided solely in the form of a counter ion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said H$_3$O$^+$ ions may be provided by the addition of an acid or an acid salt of said anion, or the addition of an acid or an acid salt which simultaneously serves to provide all or part of said excess solubilized calcium ions.

In a preferred embodiment of the preparation of the functionalized natural or synthetic calcium carbonate, the natural or synthetic calcium carbonate is reacted with the acid and/or the carbon dioxide in the presence of at least one compound selected from the group consisting of aluminium sulfates, silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural or synthetic calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or synthetic calcium carbonate while the reaction of natural or synthetic calcium carbonate with an acid and carbon dioxide has already started. Further details about the preparation of the functionalized natural or synthetic calcium carbonate in the presence of at least one silicate and/or silica and/or aluminium hydroxide and/or earth alkali aluminate component(s) are disclosed in WO 2004/083316, the content of this reference herewith being included in the present application.

The functionalized natural or synthetic calcium carbonate can be kept in suspension, optionally further stabilised by a dispersant. Conventional dispersants known to the skilled person can be used. A preferred dispersant is polyacrylic acid or partially or totally neutralized polyacrylic acid.

Alternatively, the aqueous suspension described above can be dried, thereby obtaining the solid (i.e. dry or containing as little water that it is not in a fluid form) functionalized natural or synthetic calcium carbonate in the form of granules or a powder.

In a preferred embodiment, the functionalized natural or synthetic calcium carbonate has a BET specific surface area of from 5 m$^2$/g to 200 m$^2$/g, preferably 20 m$^2$/g to 150 m$^2$/g, more preferably 40 m$^2$/g to 100 m$^2$/g, measured using nitrogen and the BET method according to ISO 9277:2010.

Furthermore, it is preferred that the functionalized natural or synthetic calcium carbonate has a weight median grain diameter of from 0.1 to 50 μm, preferably from 0.5 to 25 μm, more preferably from 0.8 to 20 μm, still more preferably from 1 to 15 μm, measured using Malvern Mastersizer X long bed.

In a preferred embodiment, the functionalized natural or synthetic calcium carbonate (FCC) has a BET specific surface area within the range of 5 m$^2$/g to 200 m$^2$/g and a weight median grain diameter within the range of 0.1 μm to 50 μm. More preferably, the specific surface area is within the range of 20 m$^2$/g to 150 m$^2$/g and the weight median grain diameter is within the range of 0.5 μm to 25 μm. Even more preferably, the specific surface area is within the range of 40 m$^2$/g to 100 m$^2$/g and the weight median grain diameter is within the range of 1 μm to 15 μm.

By the above described process natural or synthetic calcium carbonate is modified to enhance on one hand the porosity of the FCC and on the other hand to enlarge the surface area. The FCC absorbs water at a faster rate compared to conventional calcium carbonate and is able to absorb ten times more fluid than conventional calcium carbonate. Reference is made to C. J. Ridgway et al. "Modified calcium carbonate coatings with rapid absorption and extensive liquid uptake capacity", *Colloids and Surfaces A: Physicochemical and Engineering Aspects*, vol. 236, no. 1-3, pp. 91-102, April 2004.

In this respect, it is believed that because of the intra and interpore structure of the functionalized calcium carbonate, air is entrapped in the pores which promotes flotation of the particles.

Preferably, the functionalized natural or synthetic calcium carbonate has an intra-particle porosity within the range from 20 vol.-% to 99 vol.-%, preferably from 30 vol.-% to 70 vol.-%, more preferably from 40 vol.-% to 60 vol.-% calculated from a mercury porosimetry measurement. From the bimodal derivative pore size distribution curve the lowest point between the peaks indicates the diameter where the intra and inter-particle pore volumes can be separated. The pore volume at diameters greater than this diameter is the pore volume associated with the inter-particle pores. The total pore volume minus this inter particle pore volume gives the intra particle pore volume from which the intra particle porosity can be calculated, preferably as a fraction of the solid material volume, as described in *Transport in Porous Media* (2006) 63: 239-259.

Thus, the intra-particle porosity determined as the pore volume per unit particle volume is within the range of from 20 vol.-% to 99 vol.-%, preferably from 30 vol.-% to 80 vol.-%, more preferably from 40 vol.-% to 70 vol.-%, most preferably from 50 vol. % to 65 vol. %.

Due to the high porosity of the functionalized natural or synthetic calcium carbonate, on one side a significant amount of air is present in the pores, which upon contact with the gastric fluid is displaced and water as well as gastric fluid enter the pores and may start an uncontrolled decomposition of the functionalized natural or synthetic calcium carbonate thereby releasing $CO_2$. In order to prevent uncontrolled dissolution and the water and/or gastric fluid entering the pores, the functionalized natural or synthetic calcium carbonate is mixed with at least one formulating aid. Said formulating aid being at least one film forming compound and/or composition. Said compound and/or composition can be selected from hydrophilic film forming excipients or from lipophilic film forming excipients and combinations thereof, and are present in amount from about 1 wt % to about 60 wt %, preferably from about 3 wt % to about 60 wt %, more preferably from about 5 wt % to about 60 wt % based in the total weight of the formulation.

Hydrophilic film forming excipients resulting in hydrophilic formulations comprise but are not limited to water soluble polyethylene glycols, polyethylene oxides, polypropylene glycols, polypropylene oxides or combinations thereof, said polymers having a weight average molecular weight from 2,000 Da to 20,000,000 Da, Chitosan, Polymers of acrylic acid, Polyvinylpyrrolidon and its modifications (insoluble cross-linked polyvinylpyrollidones, homopolymers of N-vinyl-2-pyrrolidone), modified cellulose gums, starch glycolates, pregelatinized starch, sodium carboxymethyl starch, low-substituted hydroxypropyl cellulose, alkyl-, hydroxyalkyl-, carboxyalkyl-cellulose esters, hydroxypropyl methyl cellulose phthalate, carboxymethylcellulose salts, alginates, ion exchange resins, gums, chitin, clays, gellan gum, crosslinked polacrillin copolymers, agar, gelatin, dextrines, shellac and combinations thereof.

Lipophilic film forming excipients resulting in lipophilic formulations comprise but are not limited to hydrogenated vegetable, castor oils, mineral oils, waxes fatty acids and fatty acid salts with a carbon chain lengths from $C_6$ to $C_{20}$, being branched, un-branched, unsaturated, partially saturated, and their combinations, magnesium and/or calcium stearate, paraffin, cetyl alcohol, cetyl stearyl alcohol, glyceril monostearate, lanolin, lanolin alcohols, polyethylene glycol ethers of n-alkanols, polyoxyethylene castor oil derivates, polyoxyethylene sorbitan fatty acid esters, polyethylene stearates, sorbitan esters, stearyl alcohol, glycerol dibehenate, sodium stearyl fumarate, glycerol disteareate and combinations thereof.

The instantly floating gastroretentive formulation of the present invention may optionally further comprise at least one water soluble acid. Said water soluble acid is preferably selected from acids in solid from such as citric acid, fumaric acid, tartaric acid, or malic acid and combinations thereof. Such acid or their combinations being present in amounts of up to 10 wt %, preferably up to 8 wt %, still more preferably up to 5 wt %, based on the total weight of the formulation.

The formulation thus obtained is submitted to a compaction process, wherein the functionalized natural or synthetic calcium carbonate, the at least one pharmaceutically active ingredient or inactive precursor, formulation aids, and the optional water soluble acid, are made into granules. The granulation process can be selected from melt, dry or wet granulation process as well as roller compaction, extrusion spheronisation or hot melt extrusion. Due to the water susceptibility of the acid, wet granulation is preferably carried out using a non-water based granulation liquid. Such non-water based granulation liquid is for example ethanol 96%.

The granules obtained by any of the previously described granulation process, are instantly floating gastrorententive granules. Such granules can be dosed directly when packaged into sachets or stick packs. The granules can also be compacted into tablets or mini-tablets, or pellets. A further dosage form is in the form of capsules.

The inventors believe, without being bound by any theory, that the granules comprising the functionalized natural or synthetic calcium carbonate, mixed with a film forming agent and optionally said solid water soluble acid, the pores are covered or at least partially covered, closed or partially closed thereby trapping air inside the pore, thereby enhancing the floatability of the granules.

The optional addition of the water soluble acid is intended to provide an H+ donor when contacted with the gastric fluid. This H+ donor is believed to support the floating properties in the following way. The functionalized natural or synthetic calcium carbonate wherein the pores are partially or completely closed comprises air in the closed or partially closed pores.

Upon contact with the gastric fluid partial erosion of the functionalized natural or synthetic calcium carbonate takes place and part of the entrapped air plug may be liberated. However, due to the additional H+ donor, portions of the functionalized natural or synthetic calcium carbonate decompose further thereby liberating $CO_2$ which partially replaces the liberated air form the air plug. By this flotation is supported even with ongoing erosion of the granules.

When the granules are compacted to tablets this effect is slowed down, due to the smaller surface being accessible by the gastric fluid. As the film forming compounds and/or compositions partially protect the pores form excessive erosion from the gastric fluid and/or water, the tables will sufficiently long persist in the stomach floating on the gastric fluid. Even if the pores on the surface are eroded and filled with fluid, the buoyancy is still preserved due to the film forming compounds and/or compositions protecting the underlying pored form being prematurely eroded.

In a particular embodiment the instantly floating gastroretentive formulation is in the form of a tablet. Said tablet further comprising additional compounds such as fillers, binders, diluents, adhesives, lubricants or miscellaneous materials such as buffers and adsorbents, natural or synthetic scenting agents, natural or synthetic flavoring agents, natural or synthetic coloring agents, natural or synthetic sweeteners and/or mixtures thereof.

Suitable natural or synthetic scenting agents include one or more volatilized chemical compounds, generally at a very low concentration, that humans or other animals perceive by the sense of olfaction.

Suitable natural or synthetic flavoring agents include but are not limited to mints, such as peppermint, menthol, vanilla, cinnamon, various fruit flavors, both individual or mixed, essential oils such as thymol, eucalyptol, menthol, and methyl salicylate, allylpyrazine, methoxypyrazines, 2-isobutyl-3 methoxypyrazine, acetyl-L-pyrazines, 2-acetoxy pyrazine, aldehydes, alcohols, esters, ketones, pyrazines, phenolics, terpenoids and mixtures thereof.

The flavoring agents are generally utilized in amounts that will vary depending upon the individual flavor, and may, for example, range in amount of about 0.5% to about 4% by weight of the final composition.

Suitable natural or synthetic coloring agents include, but are not limited to, titanium dioxide, flavone dyes, isoquinoline dyes, polyene colorants, pyran colorants, naphthochinone dyes, chinone and anthrachinone dyes, chromene dyes, benzophyrone dyes as well as indigoid dyes and indole colorants. Examples thereof are caramel coloring, annatto, chlorophyllin, cochineal, betanin, turmeric, saffron, paprika, lycopene, pandan and butterfly pea.

Suitable natural or synthetic sweeteners include but are not limited to xylose, ribose, glucose, mannose, galactose, fructose, dextrose, sucrose, sugar, maltose, partially hydrolyzed starch, or corn syrup solid, and sugar alcohols such as sorbitol, xylitol, mannitol, and mixtures thereof; water soluble artificial sweeteners such as the soluble saccharin salts, i.e. sodium, or calcium saccharin salts, cyclamate salts, acesulfam-K and the like, and the free acid form of saccharin and aspartame based sweeteners such as L-aspartyl-phenyl-alanine methyl ester, Alitame® or Neotame®.

In general, the amount of sweetener will vary with the desired amount of sweeteners selected for a particular tablet composition.

Within the context of the present invention, a pharmaceutically active ingredient refers to pharmaceutically active ingredients which are of synthetic-, semi-synthetic or of natural origin or combinations thereof. Such active ingredient encompasses also inactive pharmaceutical and biological precursors which will be activated at a later stage.

The activation of such inactive precursors is known to the skilled person and commonly in use, e.g. activation in the stomach and/or gastro-intestinal pathway—such as acidic activation or tryptic- or chimotryptic cleavage.

It lies within the understanding of the skilled person that the mentioned activation methods are of mere illustrative character and are not intended to be of limiting character.

The present invention refers also to a process or a method for producing an instantly floating gastroretentive formulation comprising the steps:
a) providing a functionalized natural and/or synthetic calcium carbonate comprising mineral, wherein said functionalized natural or synthetic calcium carbonate is a reaction product of natural or synthetic calcium carbonate with carbon dioxide and one or more acids, wherein the carbon dioxide is formed in situ by the acid treatment and/or is supplied from an external source;
b) providing at least one pharmaceutically active ingredient;
c) providing at least one formulating aid;
d) mixing the compounds provided in steps a) b) and c)
e) granulating the mixture of step d)

The granulation of the instantly floating gastroretentive formulation can also be performed by roller compaction.

In the method of the present invention the source of natural calcium carbonate for preparing the functionalized calcium carbonate (FCC) is selected from the group of marble, calcite, chalk, limestone and dolomite and/or mixtures thereof.

In a particular embodiment the synthetic calcium carbonate for preparing the functionalized calcium carbonate is precipitated calcium carbonate (PCC) comprising aragonitic, vateritic or calcitic mineralogical crystals forms, especially prismatic, rhombohedral or scalenohedral PCC or mixtures thereof.

The functionalized natural or synthetic calcium carbonate used in the method of the present invention has a BET specific surface area of from 5 $m^2/g$ to 200 $m^2/g$, preferably 20 $m^2/g$ to 150 $m^2/g$, more preferably 40 $m^2/g$ to 100 $m^2/g$, measured using nitrogen and the BET method according to ISO 9277:2010.

Furthermore, it is preferred that the functionalized natural or synthetic calcium carbonate in method of the present invention has a weight median grain diameter of from 0.1 to 50 µm, preferably from 0.5 to 25 µm, more preferably from 0.8 to 20 µm, still more preferably from 1 to 15 µm, measured using Malvern Mastersizer X long bed.

In the method of the present invention the at least one pharmaceutically active ingredient or inactive precursor is selected from synthetic-, semi-synthetic or natural origin or combinations, thereof.

The activation of such inactive precursors is known to the skilled person and commonly in use, e.g. activation in the stomach and/or gastro-intestinal pathway—such as acidic activation, alkaline activation, tryptic-, chimotryptic or pepsinogenic activation by enzymatic cleavage.

The method of the present invention may be also varied in that parts of the formulation aid of step c) is first mixed with the FCC of step a) and the at least one pharmaceutically active ingredient of step b), and the remaining portion of the formulation aid is then added to the mixture, followed by the granulation step e).

In the method of the present invention, the at least one formulating aid is at least one film forming compound and/or composition.

Said compound and/or composition can be selected from hydrophilic film forming excipients or from lipophilic film forming excipients and combinations thereof, and are present in amount from about 1 wt % to about 60 wt %, preferably from about 3 wt % to about 60 wt %, more preferably from about 5 wt % to about 60 wt % based in the total weight of the formulation.

Hydrophilic film forming excipients resulting in hydrophilic formulations comprise but are not limited to water soluble polyethylene glycols, polyethylene oxides, polypropylene glycols, polypropylene oxides or combinations thereof, said polymers having a weight average molecular weight from 2,000 Da to 20,000,000 Da, Chitosan, Polymers of acrylic acid, Polyvinylpyrrolidon and its modifications (insoluble cross-linked polyvinylpyrollidones, homopolymers of N-vinyl-2-pyrrolidone), modified cellulose gums, starch glycolates, pregelatinized starch, sodium carboxymethyl starch, low-substituted hydroxypropyl cellulose, alkyl-, hydroxyalkyl-, carboxyalkyl-cellulose esters, hydroxypropyl methyl cellulose phthalate, carboxymethylcellulose salts, alginates, ion exchange resins, gums, chitin, clays, gellan gum, crosslinked polacrillin copolymers, agar, gelatin, dextrines, shellac and combinations thereof.

Lipophilic film forming excipients resulting in lipophilic formulations comprise but are not limited to hydrogenated vegetable, castor oils, mineral oils, waxes fatty acids and fatty acid salts with a carbon chain lengths from $C_6$ to $C_{20}$, being branched, un-branched, unsaturated, partially saturated, and their combinations, magnesium and/or calcium stearate, paraffin, cetyl alcohol, cetyl stearyl alcohol, glyceril monostearate, lanolin, lanolin alcohols, polyethylene glycol ethers of n-alkanols, polyoxyethylene castor oil derivates, polyoxyethylene sorbitan fatty acid esters, polyethylene stearates, sorbitan esters, stearyl alcohol, glycerol dibehenate, sodium stearyl fumarate, glycerol distearate and combinations thereof.

In the method of the present invention a water soluble acid can be added in either of the steps a), b) or c), i.e. the water soluble acid is added prior to step d). In a particular method the water soluble acid can be added in portions in either of the step a), b) and/or c).

The acid is present in amounts of up to 10 wt %, preferably up to 8 wt %, still more preferably up to 5 wt %, based on the total weight of the formulation.

The water soluble acid is preferably selected from acids in solid from such as citric acid, fumaric acid, tartaric acid, or malic acid and combinations thereof.

The present in invention refers also to the use of functionalized natural or synthetic calcium carbonate comprising mineral in instant floating gastroretentive formulations. Such formulations being made into dosage forms comprising tablets, mini-tablets, granules, capsules or pellets.

The present invention further refers to the use of functionalized natural or synthetic calcium carbonate comprising mineral in the process or method for preparing instant floating gastroretentive formulations. Such formulations being made into dosage forms comprising tablets, mini-tablets, granules, capsules or pellets.

The present invention further refers to the use of functionalized natural or synthetic calcium carbonate in instantly floating gastroretentive formulations as previously described.

The present invention further refers also to the use of functionalized natural or synthetic calcium carbonate for preparing an instantly floating gastroretentive formulation.

The present invention still further refers to tablets, mini-tablets, granules, capsules or pellets, comprising the instantly floating gastroretentive formulations of the present invention.

The present invention still further refers tablets, mini-tablets, granules, capsules or pellets, comprising the instantly floating gastroretentive formulation, wherein said formulation is obtained by the herein described methods.

The present invention is now further explained by way of the following figures and examples, which are only illustrative and are not intended to restrict the invention in any way.

DESCRIPTION OF THE FIGURES

FIG. 1b is a schematic representation of a single unit of FIG. 1a.

EXAMPLES

Preparation of FCC-Based Floating Formulations

The instantly floating gastroretentive formulation of the present invention were prepared according to table 1.

For a hydrophilic formulation (HF1), the required amount of FCC, a water soluble polyethylene oxide (Polyox™ WSR 301, form The Dow Chemical Company, USA), a low substituted hydroxypropyl methyl cellulose (Methocel® K 100 Premium LV from Sandoz Pharma AG, Switzerland) and citric acid (Acid citricum monohydr. pulvis, Hänsler AG, Switzerland) and as a model drug caffeine (Coffeiunm WSF, from Böhringer-Ingelheim, Germany) were weighted and mixed in a tumbling mixer (Turbula, type T2C, Switzerland) at room temperature, for 10 min at 33 rpm. Afterwards, ethanol (96%) was added as granulation liquid. The granulation process was carried out by slurryfication in a beaker. Ethanol was added until the mass was turning into stable, homogeneous slurry. The obtained slurry was dried and passed through a sieve (1000 µm).

For a lipophilic formulation (LF2), the required amount of FCC, a water soluble polyethylene oxide (Polyox™ WSR 301, form The Dow Chemical Company, USA), hydrogenated vegetable oil (Lubritab®, JRS Pharam, Germany), and caffeine as model drug where weighted. Prior to its use, Lubritab® was melted. FCC, caffeine and half of the melted Lubritab® was added under stirring conditions. Afterwards, Polyox™ WSR 301 and the remaining half of Lubritab® were added under stirring with magnetic stirrer. Upon cooling the stirred mass the granules were obtained due to in-situ agglomeration.

The obtained granules were passed through a sieve (1000 µm).

TABLE 1

Composition of floating compositions.

| Formulation | FCC (%, w/w) | PolyoxTM WSR 301 (%, w/w) | Methocel® K100 Premium LV (%, w/w) | Citric acid (%, w/w) | Lubritab® (%, w/w) | Caffeine (%, w/w) |
|---|---|---|---|---|---|---|
| HF1 | 56.25 | 7.50 | 10.875 | 0.375 | — | 25.00 |
| LF2 | 37.50 | 5.00 | — | — | 40.83 | 16.67 |

Preparation of Tablet Comprising the FCC-Based Floating Formulation

Instantly floating gastroretentive tablets were prepared by compacting the FCC-based floating formulation HF1 and LF2 using a single punch eccentric press (Korsch EK0, Germany) according to table 2. Resulting tablet heights were calculated to yield densities of 0.8 g/cm3 and 0.9 g/cm3 for the hydrophilic and lipophilic formulations respectively. The punch gap for compaction process was set to calculated values for HF and LF formulations respectively. Two sizes of tablets were manufactured: standard-sized and small-sized. The small-sized compacts were used as a model for mini-tablets (i.e. tablets with diameter less than 3 mm$^1$). Standard-sized tablets were flat-faced, whereas the small-sized tablets had a concave shape.

TABLE 2

Preparation of floating tablets.

| | Standard-sized tablets | | | Small-sized tablets | | |
|---|---|---|---|---|---|---|
| Formulation | amount (mg) | radius (mm) | height (mm) | amount (mg) | radius (mm) | Height (mm) |
| HF1 | 400 | 5.50 | 5.00 | 50 | 2.5 | 3.83 |
| LF2 | 600 | 5.50 | 7.00 | 75 | 2.5 | 4.54 |

The tablets were further characterized and the results are summarized in table 3.

TABLE 3

Properties of produced floating tablets.

| Formulation | weight mg | diameter mm | thickness mm | tensile strength N/mm$^2$ | porosity % | true density of floating mixture g/cm$^3$ |
|---|---|---|---|---|---|---|
| HF1 standard | 400 | 11.01 | 4.98 | 0.67 | 59 | 2.0101 |
| HF1 small s. | 50 | 5.00 | 3.83 | 1.06 | 60 | 2.0101 |
| LF2 standard | 600 | 11.01 | 6.98 | 0.17 | 37 | 1.4359 |
| LF2 small s. | 75 | 5.00 | 4.56 | 0.47 | 32 | 1.4359 |

Evaluation of In Vitro Floating Behavior and Drug Release

Figure 1A:
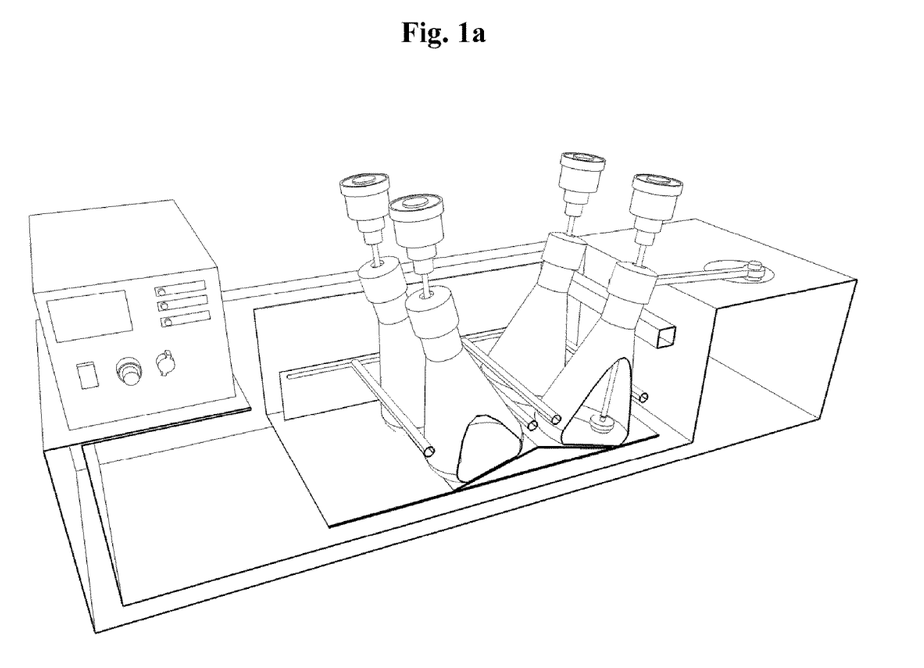
FIG. 1a is a schematic representation of the proposed stomach model method to evaluate floating behavior and drug release
Figure 1B:
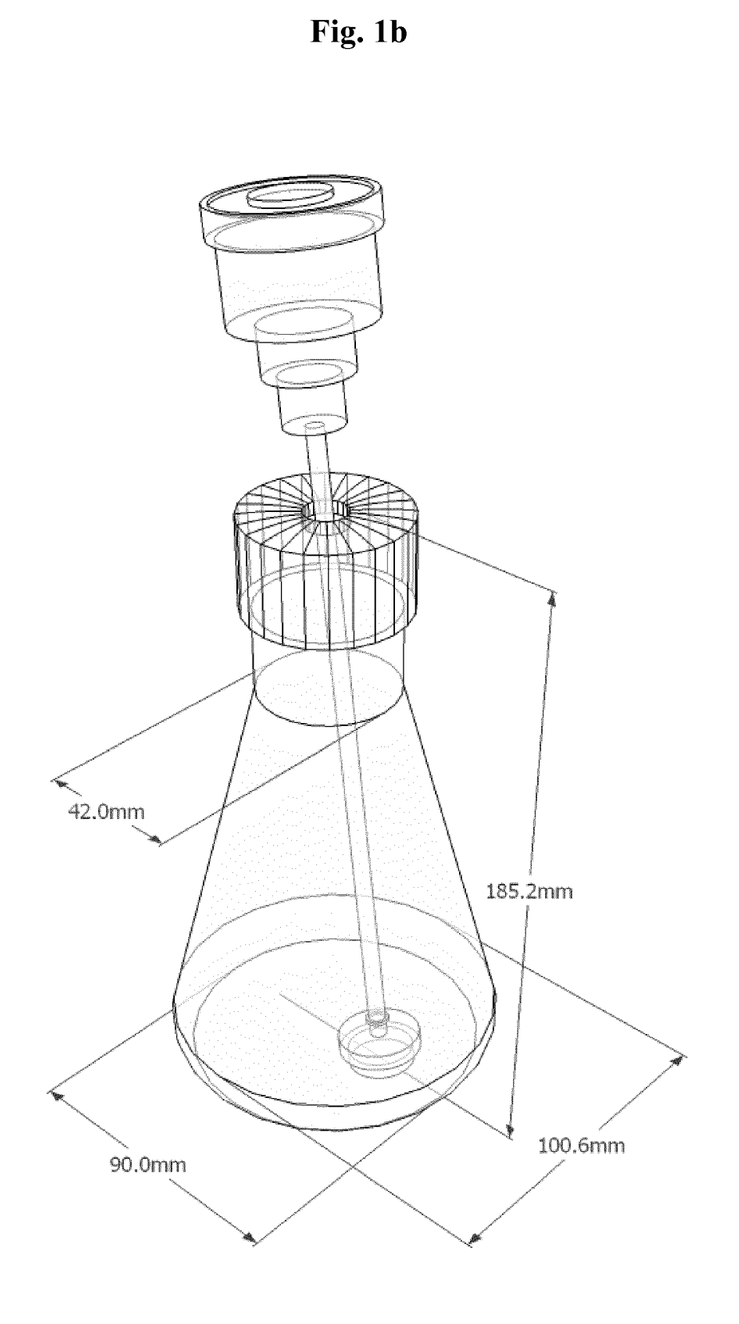

To simultaneously assess in vitro floating characteristics and drug release of tablets (n=4), a dissolution apparatus (Sotax AT7smart, Switzerland) modified according to schematics in FIG. 1 (i.e. 4 vessels were exchanged with Erlenmeyer 500 ml flasks) was used wherein the experimental setup (FIG. 1) consisted of 4 polycarbonate Erlenmeyer flasks (500 ml) which were fixed on the carriage of a water bath shaker (Kobrin Scientific precision centigrade temperature processor 345, Switzerland). The carriage moved horizontally with rotation speed of 75 rpm and amplitude of 50 mm. Measurement was performed using 400 ml 0.1 N HCl as test media at a temperature of 37° C.

For comparison, floating behavior and drug release (n=3) were analyzed using USP dissolution apparatus II (Sotax AT 7 smart, Switzerland). Measurement was done in 900 ml 0.1 N HCl with paddle rotation of 100 rpm and at temperature of 37±0.5° C.

Drug content was analyzed in the dissolution media at predetermined time intervals using UV/Vis spectrophotometer at 272 nm (Perkin Elmer Lambda 25, USA). The UV absorption spectrum of caffeine exhibits a pair of absorption bands peaking at 205 nm and 273 nm with a characteristic absorption shoulder between them.

Typically, caffeine content is determined by measuring the absorbance near the 273 nm peak.

Floating lag time of reference is defined as time a tablet needed to rise to the surface of the test medium after placing it into the test medium and floating duration noted as total time a tablet constantly floated on the surface of the test medium were visually observed.

Figure 2:
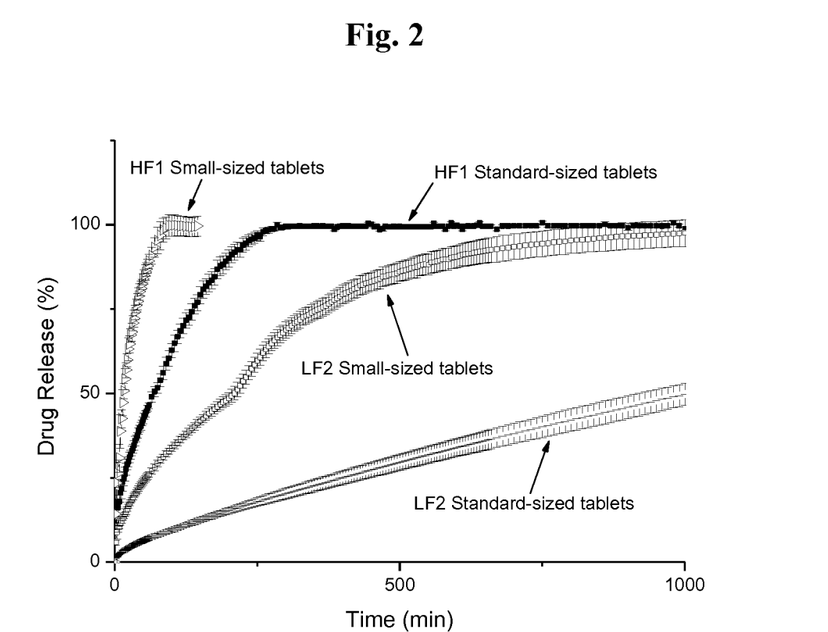
FIG. 2 shows caffeine release profiles of small-sized and standard-sized tablets of floating formulation HF1 and LF2.

Caffeine release profiles of floating tablets of hydrophilic and lipophilic formulation are displayed in FIG. 2. Standard-sized tablets of both formulations showed instant flotation. In case of formulation HF1, compacts were floating for 5 h and eroded completely within this time while releasing drug substance and stay afloat. For lipophilic formulation LF2, it was observed that floating times were of several days. After complete release of model drug, a lipophilic matrix remained. Drug release mechanism of the two types of floating formulations differs: erosion-controlled for formulation HF1 and diffusion-controlled for hydrophobic formulation LF2. For hydrophilic floating tablets, all of the caffeine was released after 5 h, while for lipophilic formulations complete drug release was detected after 59 h 45 min.

FIG. 2 further illustrates drug release profiles of small-sized floating tablets of formulation HF1 and LF2. No floating lag times were observed for both formulations. For compacts of hydrophilic formulation HF1, floating times of 90 min were measured and tablets dissolved completely.

Drug release mechanism was classified as erosion-controlled; after 90 min 100% caffeine release was achieved. Small-sized tablets of formulation LF2 were floating for several days and a lipophilic tablet matrix was retained. Drug release was diffusion-controlled; after 17 h drug substance was completely released. Release profile (FIG. 2) of formulation LF2 shows disintegration of small-sized floating tablets at 210 min.

Comparison of Stomach Model and USP Dissolution Apparatus II

Figure 3:
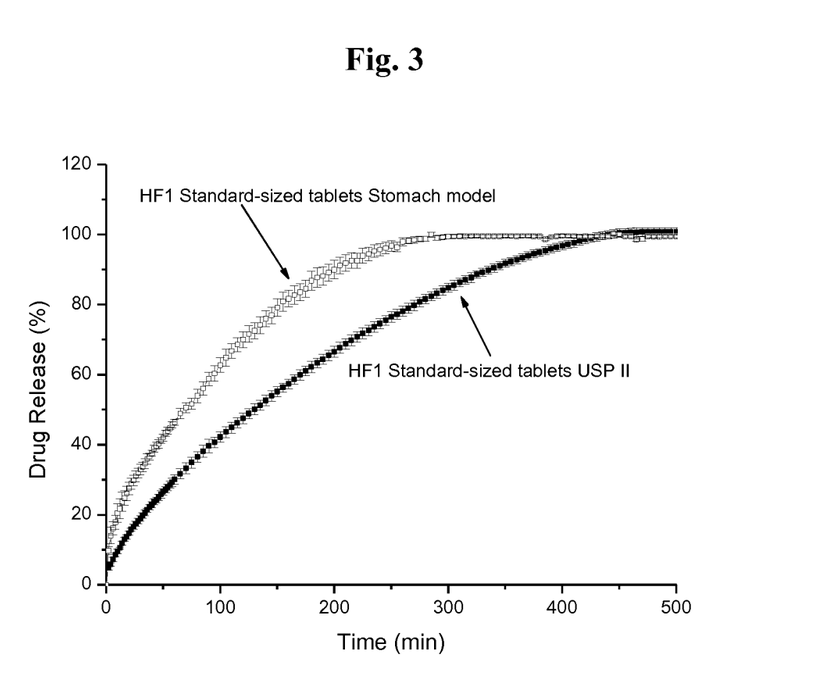
FIG. 3 shows a comparison of caffeine release profiles of standard-sized floating tablets tested using stomach model and USP dissolution apparatus II.

FIG. 3 compares the drug release of floating tablets measured using the custom-built stomach model (schematic of stomach model apparatus is shown in FIG. 1) with the conventional USP dissolution apparatus II. Dissolution testing by USP paddle method resulted in a slowdown of caffeine release; 100% drug substance was released after 470 min. During measurement the FCC-based tablets were floating on test media surface and rotating around the paddle shaft. Using the stomach model method, complete caffeine release of standard-sized tablets of formulation HF1 was assessed after 300 min. Due to horizontal movement of the shaker, floating tablets were fully immersed in the dissolution media and drying of the tablet surface was avoided.

In Vitro Drug Release of FCC-Based Floating Tablets

In vitro testing of FCC-based tablets showed that manufacturing of floating tablets with different release profiles is possible. Small-sized tablets were releasing drug faster. This could be explained by their higher surface area. It was further observed that the size effect was independent of the formulation type (i.e. lipophilic or hydrophilic). In case of hydrophilic tablet formulation disintegration did not happen; this supports the hypothesis of erosion-controlled drug release mechanism. Small-sized lipophilic tablets disintegrated at 210 min. The alteration of the release profile is supporting the hypothesis of diffusion-controlled release mechanism from lipophilic formulations.

FCC for the Preparation of Floating Tablets

FCC seems to be a promising new pharmaceutical excipient for preparation of floating tablets. Due to its highly porous structure and lamellar surface it is possible to manufacture compacts which have a density less than unity and are instantly floating. The prepared floating tablets exhibited no floating lag time and hence a reduced risk for unpredictable and premature gastric emptying. Furthermore, FCC-based floating tablets showed a sufficient hardness to resist destruction by gastric peristalsis and to be further processible.

Two floating formulations—hydrophilic and hydrophobic—were prepared. According to results of preliminary trials, a granulation step seemed to be necessary for production of FCC-based floating formulations to improve flowability and fillability of the mixtures into the die of the tablet press.

Caffeine release profiles showed that lipophilicity of the formulation influenced drug release rate as well as drug release mechanism. Tablet size affected drug release rate, but did not have an influence on release mechanism.

Custom-Built Stomach Model

Stomach model showed good performance to overcome the limitations of the standard methods. The floating tablets were not drying on the surface due to continuous shaking of the dissolution vessels. Absence of rotating elements excluded the effects observed in USP dissolution apparatus I and II. In addition, there was no need to force the tablets under the liquid surface, hence simplifying the construction of the stomach model. During the test the dissolution media was protecting the tablets from significant impacts with solid construction elements.

In comparison to traditional in vitro dissolution testing by USP apparatus I or II, the proposed stomach model offers the possibility to investigate drug release of floating delivery devices with taking into account gastric motility. Therefore the conclusion is that the new method might be able to predict with higher accuracy in vivo behavior of floating tablets.

Measurement Methods

True Density

The true density of FCC was determined by helium pycnometry (Micromeritics AccuPyc 1330, USA).

BET Specific Surface Area

To measure the specific surface area, a Nova 2000e (Quantachrome Instruments, USA) was used with the five point BET method. After degassing the samples for 12 hours at room temperature, the samples were measured with nitrogen at constant temperature (77.4 K). The measurement was performed in duplicate.

Particle Size Distribution

Particle size distribution was determined with a Mastersizer X long bed (Malvern Instruments, UK). FCC particles were dispersed in isopropyl myristate and then analyzed (separately) by using the small volume sample presentation unit (Malvern Instruments, UK). The samples were measured in triplicate.

Characterization of FCC-Based Floating Tablets

Mean tablet weight (n=7) was measured with an electronic balance (Mettler Toledo AX204 Delta Range, Switzerland). Determination of tablet diameter (n=7) and tablet thickness (n=7) was done using a dial indicator (Mitutoyo Model CD-15CPX, Japan). Helium pycnometry (Micromeritics AccuPyc 1330, USA) was performed to measure true density. The porosity ε of flat-faced tablets was calculated according to the following equation (1):

$$\varepsilon = \left(1 - \frac{\frac{m}{\rho}}{\pi \cdot r^2 \cdot h}\right) \cdot 100 \quad (1)$$

wherein m is the tablet weight, ρ is the true density of the powder mixture, r is the tablet radius, and h is the tablet height. Porosity ε of concave-shaped compacts was calculated as follows:

$$\varepsilon = \left(1 - \frac{\frac{m}{\rho}}{\pi \cdot r^2 \cdot w + 2\left(\frac{\pi \cdot h_{cap}}{6} \cdot (3r^2 + h_{cap}^2)\right)}\right) \cdot 100 \quad (2)$$

wherein m is the tablet weight, ρ is the true density of the powder mixture, r is the tablet radius, w is the central cylinder thickness, and $h_{cap}$ is the height of the spherical cap.

A hardness tester (Tablet Tester 8M, Switzerland) was used to analyze tablet breaking strength (n=3). Afterwards, tablet tensile strength, σ (MPa) was calculated according to equation 3 and 4 for flat-faced and concave-shaped tablets, respectively.

$$\sigma_t = \frac{2 \cdot F}{\pi \cdot d \cdot h} \quad (3)$$

wherein F is the diametrical crushing force, d is the tablet diameter, and h is the tablet height.

$$\sigma_t = \frac{10 \cdot F}{\pi \cdot d^2} \cdot \left(2.84 \cdot \frac{h}{d} - 0.126 \cdot \frac{h}{w} + 3.15 \cdot \frac{w}{d} + 0.01\right)^{-1} \quad (4)$$

wherein F is the diametrical crushing force, d is the tablet diameter, h is the tablet height, and w is the central cylinder thickness.

UV/VIS Measurements

Drug content was analyzed online in the dissolution media at predetermined time intervals using UV/Vis spectrophotometer at 272 nm (Perkin Elmer Lambda 25, USA). The UV absorption spectrum of caffeine exhibits a pair of absorption bands peaking at 205 nm and 273 nm with a characteristic absorption shoulder between them. Typically, caffeine content is determined by measuring the absorbance near the 273 nm peak.

The invention claimed is:

1. An instantly floating gastroretentive formulation comprising at least one functionalized natural and/or synthetic calcium carbonate comprising pores containing air that promote flotation of the formulation in gastric fluid, at least one pharmaceutically active ingredient, and at least one film forming excipient, wherein the functionalized natural or synthetic calcium carbonate is a reaction product of natural or synthetic calcium carbonate with carbon dioxide and one or more acids, wherein the carbon dioxide is formed in situ by the acid treatment and/or is supplied from an external source, wherein the functionalized natural or synthetic calcium carbonate is made before the formulation is prepared, wherein the formulation comprises 30 to 95 weight percent of the at least one functionalized natural and/or synthetic calcium carbonate based on the total weight of the formulation, wherein the formulation comprises 1 to 60 wt % of the at least one film forming excipient based on the total weight of the formulation, and wherein the formulation prior to administration has a density that is below the density of gastric fluid.

2. The formulation according to claim 1, wherein the functionalized calcium carbonate (FCC) is prepared from natural calcium carbonate selected from the group consisting of marble, calcite, chalk, limestone, dolomite, and any mixture thereof.

3. The formulation according to claim 1, wherein the functionalized calcium carbonate (FCC) is prepared from synthetic calcium carbonate that is precipitated calcium carbonate (PCC) having one or more aragonitic, vateritic, prismatic, rhombohedral or scalenohedral forms.

4. The formulation according to claim 1, wherein the one or more acids is selected from the group consisting of hydrochloric acid, sulfuric acid, sulfurous acid, hydrosulfate, phosphoric acid, phosphoric acid in combination with acetic, formic or citric acid or acid salts thereof, and any mixture thereof.

5. The formulation according to claim 1, wherein the one or more acids is phosphoric acid.

6. The formulation according to claim 1, wherein the functionalized natural or synthetic calcium carbonate has a BET specific surface area of from 5 m²/g to 200 m²/g, measured using nitrogen and the BET method according to ISO 9277:2010.

7. The formulation according to claim 1, wherein the functionalized natural or synthetic calcium carbonate has a BET specific surface area of from 20 m²/g to 150 m²/g, measured using nitrogen and the BET method according to ISO 9277:2010.

8. The formulation according to claim 1, wherein the functionalized natural or synthetic calcium carbonate has a BET specific surface area of from 40 m²/g to 100 m²/g, measured using nitrogen and the BET method according to ISO 9277:2010.

9. The formulation according to claim 1, wherein the functionalized natural or synthetic calcium carbonate has a weight median grain diameter of from 0.1 to 50 μm, measured using Malvern Mastersizer X long bed.

10. The formulation according to claim 1, wherein the functionalized natural or synthetic calcium carbonate has a weight median grain diameter of from 0.5 to 25 μm, measured using Malvern Mastersizer X long bed.

11. The formulation according to claim 1, wherein the functionalized natural or synthetic calcium carbonate has a weight median grain diameter of from 0.8 to 20 μm, measured using Malvern Mastersizer X long bed.

12. The formulation according to claim 1, wherein the functionalized natural or synthetic calcium carbonate has a weight median grain diameter of from 1 to 15 μm, measured using Malvern Mastersizer X long bed.

13. The formulation according to 36, wherein the least one pharmaceutically active ingredient is an active agent or an inactive precursor that is synthetic-, semi-synthetic or of natural origin or any combination thereof.

14. The formulation according to claim 1, wherein the at least one film forming excipient is selected from the group consisting of hydrophilic film forming excipients, lipophilic film forming excipients, and any combination thereof.

15. The formulation according to claim 1, wherein the at least one film forming excipient is a hydrophilic film forming excipient selected from group consisting of water soluble polyethylene glycols, polyethylene oxides, polypropylene glycols, polypropylene oxides or any combination thereof, polymers having a weight average molecular weight from 2,000 Da to 20,000,000 Da, chitosan, polymers of acrylic acid, polyvinylpyrrolidon, insoluble cross-linked polyvinylpyrrollidones, homopolymers of N-vinyl-2-pyrrolidone, modified cellulose gums, starch glycolates, pregelatinized starch, sodium carboxymethyl starch, low-substituted hydroxypropyl cellulose, alkyl-, hydroxyalkyl-, carboxyalkyl-cellulose esters, hydroxpropyl methyl cellulose phthalate, carboxymethylcellulose salts, alginates, ion exchange resins, gums, chitin, clays, gellan gum, crosslinked polacrillin copolymers, agar, gelatin, dextrines, shellac, and any combination thereof.

16. The formulation according to claim 1, wherein the at least one film forming excipient is a lipophilic film forming excipient selected from the group consisting of hydrogenated vegetable, castor oils, mineral oils, waxes fatty acids and fatty acid salts with a carbon chain lengths from C6 to C20, being branched, un-branched, unsaturated, partially saturated, and any combination thereof, magnesium and/or calcium stearate, paraffin, cetyl alcohol, cetyl stearyl alcohol, glyceril monostearate, lanolin, lanolin alcohols, polyethylene glycol ethers of n-alkanols, polyoxyethylene castor oil derivates, polyoxyethylene sorbitan fatty acid esters, polyethylene stearates, sorbitan esters, stearyl alcohol, glycerol dibehenate, sodium stearyl fumarate, glycerol distearate, and any combination thereof.

17. The formulation according to claim 1, further comprising a water soluble solid acid.

18. The formulation according to claim 17, wherein the water soluble solid acid is selected from the group consisting of citric acid, fumaric acid, tartaric acid, malic acid, and any combination thereof.

19. A tablet, granule, capsule or pellet comprising the instantly floating gastroretentive formulation of claim 1.

20. The formulation according to claim 1, comprising 3 to 60 wt % of the least one film forming excipient based on the total weight of the formulation.

21. The formulation according to claim 1, comprising 5 to 60 wt % of the least one film forming excipient based on the total weight of the formulation.

\* \* \* \* \*